(12) United States Patent
Douthat et al.

(10) Patent No.: US 10,993,624 B2
(45) Date of Patent: May 4, 2021

(54) SYSTEMS AND METHODS FOR THERMOACOUSTIC TRANSDUCER OPTIMIZATION

(71) Applicant: ENDRA Life Sciences Inc., Ann Arbor, MI (US)

(72) Inventors: Dean Zahn Douthat, Saline, MI (US); Jang Hwan Cho, Ann Arbor, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 16/279,608

(22) Filed: Feb. 19, 2019

(65) Prior Publication Data
US 2020/0264305 A1    Aug. 20, 2020

(51) Int. Cl.
*A61B 5/00* (2006.01)
*A61B 8/00* (2006.01)
*G01S 15/89* (2006.01)

(52) U.S. Cl.
CPC .......... *A61B 5/0095* (2013.01); *A61B 8/4483* (2013.01); *A61B 8/4416* (2013.01); *A61B 2576/00* (2013.01); *G01S 15/8906* (2013.01)

(58) Field of Classification Search
CPC ............... G01S 15/899; G01S 15/8906; G01S 15/8915; A61B 8/4416; A61B 8/4477;
(Continued)

(56) References Cited

U.S. PATENT DOCUMENTS 6,216,025 B1    4/2001  Kruger
6,567,688 B1 *  5/2003  Wang ................... A61B 5/0095
                                                    600/407
(Continued)

FOREIGN PATENT DOCUMENTS

WO    2018236748 A1    12/2018

OTHER PUBLICATIONS

Valeriy G. Andreev, Alexander A. Karabutov, and Alexander A. Oraevsky; "Detection of Ultrawide-Band Ultrasound Pulses in Optoacoustic Tomography"; IEEE transactions on ultrasonics, ferroelectrics, and frequency control, vol. 50, No. 10, pp. 1383-1390, Oct. 2003.

(Continued)

*Primary Examiner* — Bill Thomson
*Assistant Examiner* — Younhee Choi
(74) *Attorney, Agent, or Firm* — Stanley E. Jelic

(57) ABSTRACT

A method and system optimize a thermoacoustic transducer functionality that is utilized in a thermoacoustic imaging system. The method and system select a pre-determined transducer geometry for the thermoacoustic imaging system, utilize the thermoacoustic imaging system with the pre-determined transducer geometry to generate at least one impulse in a field of view, acquire data from the impulse, reconstructing the data to generate N-dimensional impulse responses based upon respective channel responses, respective view responses, and a function of the acquired data, utilize the N-dimensional transforms for each image to generate a value for the pre-determined transducer functionality, and utilize the value for the pre-determined transducer functionality to determine an optimum thermoacoustic transducer functionality.

7 Claims, 11 Drawing Sheets

(58) Field of Classification Search
CPC ... A61B 8/4483; A61B 8/5261; A61B 5/0507; A61B 5/7203; A61B 5/7253; A61B 2562/0204; A61B 5/0093; A61B 5/0095; G01N 29/2431
See application file for complete search history.

(56) References Cited

U.S. PATENT DOCUMENTS

| | | | | |
|---|---|---|---|---|
| 8,499,635 | B2* | 8/2013 | Klessel | G01S 7/52028 310/322 |
| 8,998,813 | B2* | 4/2015 | Nakagawa | G01S 15/8977 600/443 |
| 2010/0017142 | A1* | 1/2010 | Watson | A61B 5/0261 702/19 |
| 2010/0082506 | A1 | 4/2010 | Avinash et al. | |
| 2013/0116538 | A1* | 5/2013 | Herzog | A61B 8/4254 600/407 |
| 2013/0303909 | A1* | 11/2013 | Kang | A61B 5/0095 600/443 |
| 2016/0178583 | A1* | 6/2016 | Ntziachristos | G01N 29/2412 73/643 |
| 2017/0311808 | A1* | 11/2017 | Thornton | A61B 5/0035 |
| 2018/0206826 | A1* | 7/2018 | Thornton | A61B 8/4488 |
| 2018/0323571 | A1* | 11/2018 | Brown | H01S 3/10069 |

OTHER PUBLICATIONS

Neda Davoudi, Xosé Luís Deán-Ben, and Daniel Razansky; "Deep learning optoacoustic tomography with sparse data"; Nature Machine Intelligence; published online Sep. 16, 2019; https://doi.org/10.1038/s42256-019-0095-3.

Sergey A. Ermilov, Tuenchit Khamapirad, Andre Conjusteau, Morton H. Leonard, Ron Lacewell, Ketan Mehta, Tom Miller, Alexander A. Oraevsky; "Laser optoacoustic imaging system for detection of breast cancer"; Journal of Biomedical Optics 14(2), 024007, pp. 024007-1 through 024007-14, Mar./Apr. 2009, published online Mar. 6, 2009. http://biomedicaloptics.spiedigitallibrary.org/.

Robert A. Kruger, William L. Kiser Jr., Daniel R. Reinecke, and Gabe A. Kruger; "Thermoacoustic computed tomography using a conventional linear transducer array"; Medical Physics vol. 30, pp. 856-860, (May 2003); doi: 10.1118/1.1565340.

Elena Merčep, Gency Jeng, Stefan Morscher, Pai-Chi Li, and Daniel Razansky; "Hybrid Optoacoustic Tomography and Pulse-Echo Ultrasonography Using Concave Arrays"; IEEE Transactions on Ultrasonics, Ferroelectrics, and Frequency Control, vol. 62, No. 9, Sep. 2015, pp. 1651-1661.

Idan Steinberg, David M. Huland, Ophir Vermesh, Hadas E. Frostig, Willemieke S. Tummers, and Sanjiv S. Gambhir; "Photoacoustic clinical imaging"; Photoacoustics 14 (2019) 77-98; published online Jun. 8, 2019. https://doi.org/10.1016/j.pacs.2019.05.001.

* cited by examiner

SYSTEMS AND METHODS FOR THERMOACOUSTIC TRANSDUCER OPTIMIZATION

FIELD

This application relates to systems and methods for thermoacoustic transducer optimization.

BACKGROUND

Thermoacoustic images are obtained by acquiring time-domain signals from individual transducer elements in an ultrasound detection array, then by applying various signal processing methods aimed at reconstructing the absorption distribution within the object of interest while reducing noise and other imaging artifacts. Most thermoacoustic image reconstruction techniques are derived from methods originally developed for other imaging modalities, such as conventional ultrasound and computed tomography (CT) and therefore are not optimized for thermoacoustic data. For instance, a typical thermoacoustic image reconstruction algorithm involves (i) deconvolving the transducer time-series data to obtain a heat absorption projection, (ii) filtering projection data to reduce blurring effects (Shepp-and-Logan filter or similar), and finally (iii) performing back-projections over all transducer elements to reconstruct the absorption distribution.

One problem associated with this approach is that commonly used time-domain filters like ramp or Shepp-and-Logan filters assume having "complete" tomographic data (a large set of image views). This assumption may not hold for thermoacoustic imaging, where only a small number of views may be sufficient for reconstructing tomographic images. Thus, applying the above-mentioned filters on a data set with a limited number of views may result in severe artifacts degrading the quality of the image. Hence, a thermoacoustic image reconstruction method is needed that uses a limited number of views to generate a clear image.

Further, a thermoacoustic imaging system may select from one of various different transducer element geometries. When adding new transducer elements, the options for which geometry to use becomes even less clear. Conventional attempts allow for manually configuring and testing a transducer element geometry by constructing thermoacoustic imaging systems with those parameters. But such manual construction is inefficient, expensive, does not contemplate as many options, and does not accurately compare to a reference.

SUMMARY

Methods and systems described herein attempt to overcome the deficiencies of the conventional solutions by optimizing thermoacoustic transducer functionality to determine a distribution, selection of transducer elements, frequency, bandwidth, and other parameters. Because of the various trade-offs and variations in selecting the thermoacoustic transducer functionality, the process is iterated using different configurations that are compared to particular metrics or an ideal system. While an ideal system may have 100 transducer elements but the restrictions allow only 30 transducer elements to be used, the methods will use simulations of various configurations to identify how to configure those 30 transducer elements to achieve desirable quality.

In one embodiment, a method for optimizing a thermoacoustic transducer of a thermoacoustic imaging system comprises generating, by a processor, at least one impulse in a field of view using a selected transducer functionality; acquiring, by the processor, data from the impulse; reconstructing, by the processor, the data to generate N-dimensional impulse responses based upon respective channel responses, respective view responses, and a function of the acquired data; generating, by the processor, N-dimensional transforms; generating, by the processor, a value for the pre-determined transducer functionality utilizing the N-dimensional transforms; automatically iterating, by the processor, a simulation using a second selected transducer functionality; and configuring, by the processor, an optimum thermoacoustic transducer functionality for at least the selected transducer functionality and the second selected transducer functionality, whereby the optimum thermoacoustic transducer functionality comprises the highest value.

In one method embodiment, the method further comprises denoising and correcting with algorithms to generate corrected time-series data for each transducer, immediately after the recording step.

In one method embodiment, the method further comprises deconvolving the corrected time-series data of a transducer element specific kernel and applying 2-D denoising and artifact correction algorithms to generate corrected deconvolved time-series data, immediately after the deconvolving step.

In one method embodiment, the transducer element specific kernels are generated by the steps comprising: estimating an impulse response for each transducer element; filtering the estimated impulse responses based upon prior transducer element knowledge; and applying 1-dimensional noise and artifact reduction to the filtered estimated impulse responses.

In one method embodiment, the prior transducer element knowledge is selected from the group consisting of a bandwidth of each transducer element in the thermoacoustic imaging system, a center frequency of each transducer element in the thermoacoustic imaging system, transducer directivity, a value derived from a noise test, or some combination thereof.

In one embodiment, the N-dimensional transform utilizes all of the acquired data.

In one method embodiment, the N-dimensional transform utilizes a subset of the acquired data.

In one method embodiment, the value defines an absolute metric which measures a quality of the N-dimensional transform without using a reference.

In one method embodiment, the value defines a relative metric that utilizes an ideal transducer functionality.

In one method embodiment, the transducer functionality is dependent upon directivity, a center frequency, and a bandwidth.

In one method embodiment, the transducer functionality is dependent upon a number of transducer elements, a distribution of transducer elements, or an orientation of transducer elements.

In one method embodiment, the transducer functionality is dependent upon a motion of transducer elements, further wherein the motion of transducer elements comprises a rotational angle and an angle step size.

In one embodiment, a system to optimize a thermoacoustic transducer geometry that is utilized in a thermoacoustic imaging system comprises: at least one radio-frequency source configured to direct pulses of radio-frequency electromagnetic radiation toward a region of interest and induce thermoacoustic signals from the region of interest; at least one thermoacoustic transducer element configured to receive the thermoacoustic signals from the region of interest; and a processor configured to accept data from the at least one radio-frequency source and the at least one thermoacoustic transducer element, wherein the processor is further configured to select a pre-determined transducer geometry for the thermoacoustic imaging system, utilize the thermoacoustic imaging system with the pre-determined transducer geometry to generate at least one impulse in a field of view, acquire data from the impulse, reconstruct the data to generate N-dimensional impulse responses based upon respective channel responses, respective view responses, and a function of the acquired data, utilize the N-dimensional impulse responses for each image to generate a value for the pre-determined transducer functionality; and utilize the value for the pre-determined transducer functionality to determine an optimum thermoacoustic transducer functionality.

In one system embodiment, the processor is further configured to denoise and correct with algorithms to generate corrected time-series data for each transducer, immediately after recording time-series data for each respective transducer element in the thermoacoustic imaging system.

In one system embodiment, the processor is further configured to deconvolve time-series data transducer element specific kernels for each respective transducer element in the thermoacoustic imaging system, then immediately apply two-dimensional denoising and artifact correction algorithms to generate corrected deconvolved time-series data.

In one system embodiment, the processor is further configured to generate the transducer element specific kernels by the steps comprising: estimating an impulse response for each transducer element; filtering the estimated impulse responses based upon prior transducer element knowledge; and applying 1-dimensional noise and artifact reduction to the filtered estimated impulse responses.

In one system embodiment, the prior transducer element knowledge is selected from the group consisting of a bandwidth of each transducer element in the thermoacoustic imaging system, a center frequency of each transducer element in the thermoacoustic imaging system, transducer directivity, a value derived from a noise test, or some combination thereof.

In one system embodiment, the N-dimensional impulse response utilizes all of the acquired data.

In one system embodiment, the N-dimensional impulse response utilizes a subset of the acquired data.

In one system embodiment, the value defines an absolute metric which measures a quality of the N-dimensional impulse response without using a reference.

In one system embodiment, the value defines a relative metric that utilizes an ideal transducer functionality.

In one system embodiment, the transducer functionality is dependent upon directivity, a center frequency, and a bandwidth.

In one system embodiment, the transducer functionality is dependent upon a number of transducer elements, a distribution of transducer elements, or an orientation of transducers.

In one system embodiment, the transducer functionality is dependent upon a motion of transducers, further wherein the motion of transducer elements comprises a rotational angle and an angle step size.

BRIEF DESCRIPTION OF THE DRAWINGS

Embodiments will now be described more fully with reference to the accompanying drawings.

DETAILED DESCRIPTION OF THE EMBODIMENTS

Figure 1:
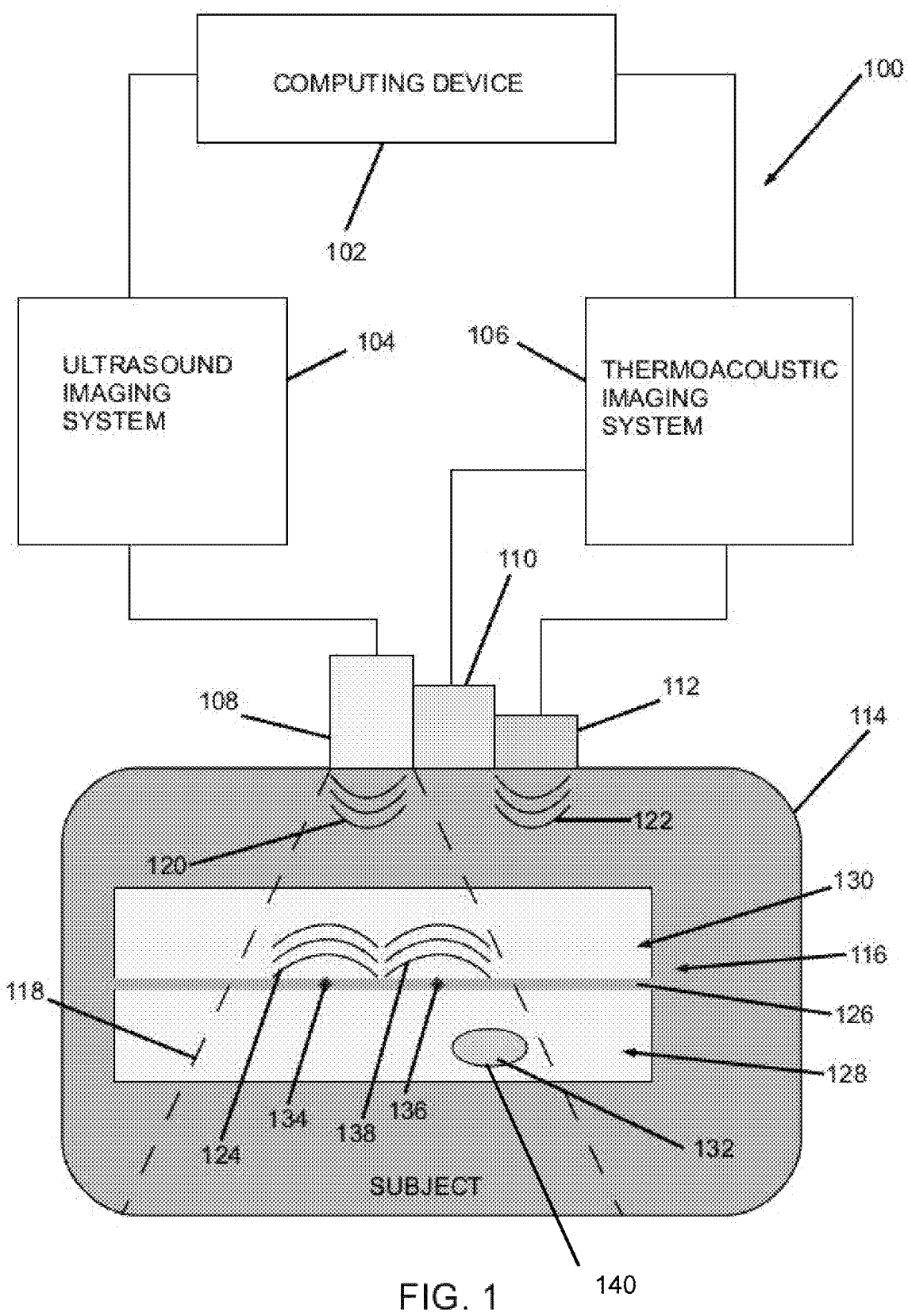
FIG. 1 shows an imaging system embodiment.

The present disclosure discusses a method to optimize thermoacoustic transducer functionality. The focus is not designing the transducer element itself, although its characteristics will be included in the design method. Rather, optimized thermoacoustic transducer functionality defines the transducer geometry, the arrangement of the transducer elements, or distribution of the transducer elements. The method described in this disclosure will select a configuration of transducer elements based on their characteristics and distribute them in a way that maximizes the sampling condition for the target within the field of view. The method will consider parameters, such as, but not limited to selecting appropriate transducer elements, frequency, and bandwidth. In an ideal scenario, an unlimited amount of transducer elements may be used, but in a configuration limited by space, cost, and other restrictions, the methods described herein can determine how to distribute the limited amount of transducer elements and which transducer elements to use.

There are many ways to optimize an ultrasound transducer. However, the methods for optimizing a transducer for conventional ultrasound imaging may not be best for the transducers that are used in other modalities, such as photoacoustic or thermoacoustic devices. Typical ultrasound transducer optimization will focus on characterizing the center frequency and the bandwidth of the transducer element. Only a few simple "geometries" are typically considered for transducers used in conventional ultrasound imaging: linear, curved, flat. But for photoacoustic or thermoacoustic imaging, more geometries are possible. Depending on the purpose and the application, the conventional ultrasound geometries may be insufficient for desirable imaging results, thereby making it difficult or impossible to extract necessary information about a patient or object.

The present disclosure focuses on photoacoustic and thermoacoustic imaging modalities and not ultrasound imaging devices (e.g., conventional ultrasound, ultrasound tomography). There are several differences between the transducers used in conventional ultrasound imaging and photoacoustic/thermoacoustic imaging modalities. First, transducers used in photoacoustic and thermoacoustic devices operate only in receive mode, not transmit-receive mode. Second, wider bandwidth is more critical to these devices. Third, the image reconstruction process is different. The key factor that needs to be considered for these modalities is the sampling condition in the field of view. Unlike ultrasound imaging, which can generate decent images with very limited view angles, photoacoustic and thermoacoustic imaging require more view angles. Tomographic imaging is required to obtain good image quality. There exist photoacoustic and thermoacoustic devices that only use very limited (mostly single) views, but their application is limited and their image quality is very poor. Therefore, designing a system with good sampling conditions is very crucial to image quality.

The present disclosure presents a method to optimize the transducer geometry of a photoacoustic or thermoacoustic system to achieve sufficient sampling conditions. The general method is as follows: an object that can be considered as an impulse is placed in the field of view; either by using a simulation or an actual acquisition, measurements are collected; for each view of collected measurements, an N-dimensional transform or impulse response is calculated (e.g., N-dimensional k-space) (reconstruction of the object using only the specific view is performed before calculating the frequency response); sampling in k-space for each view is estimated from this impulse response; and testing different combinations of the transducer geometry and element characteristics and choosing the combination that gives the best results. Alternately, based on the k-space sampling, desired geometry or element characteristics can be estimated. This method can be performed for a single view or a collection of views. For the tomographic reconstruction, the combined k-space sampling for the entire collection of views should be optimized.

The above method can be performed for the impulse object placed at a different location within the field of view. Depending on the system, each impulse location may have different optimal transducer geometry. All of such geometries will be combined based on the purpose of the system. Potential transducer geometries include but are not limited to: a bowl shape, ball shape, partial circle (C-shape), irregular locations on flat or curved lines, and random locations within a restricted area or volume.

As an alternate method to assess the sampling condition, the following steps can be used: k-space sampling; converting to spherical coordinate; measuring radial length of each frequency component based on thresholding; and evaluating the distribution of the radial length (how uniform is the radial length distribution, which angles lack sampling, etc.).

In a separate embodiment, a method to optimize the transducer geometry of a photoacoustic or thermoacoustic system to achieve good sampling conditions comprises: using more than a minimum number of transducers with more than a sufficient number of transducer characteristics; removing or adjusting transducer characteristics to meet limitations and achieve an improved system response; comparing the improved system response to an ideal response; and repeating said removing and said comparing steps until the improved ideal response matches the desired response.

In a separate embodiment, a method to optimize the transducer geometry of a photoacoustic or thermoacoustic system to achieve good sampling conditions comprises: optimizing the system until selected predefined system characteristics are satisfied. Examples of system characteristics include but are not limited to sampling.

Turning now to FIG. 1, an imaging system is shown and is generally identified by reference numeral 100. In this embodiment, the imaging system 100 comprises a computing device 102 communicatively coupled to an ultrasound imaging system 104 and a thermoacoustic imaging system 106. The ultrasound imaging system 104 and thermoacoustic imaging system 106 are configured to obtain ultrasound image data and thermoacoustic data, respectively, of a region of interest 116 associated within a subject 114. In the embodiment depicted in FIG. 1, the region of interest 116 comprises first reference 130, first boundary 126, second boundary 140, first boundary location 134, second boundary location 136, object of interest 128, and secondary object of interest (or tumor) 132.

The computing device 102 in this embodiment is a machine comprising a personal computer or other suitable processing device comprising, for example, a processing unit comprising one or more processors, non-transitory system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse, stylus, touchscreen, and/or a keyboard (not shown) are coupled to the computing device 102 for receiving user input. A display device (not shown), such as a computer screen or monitor, is coupled to the computer device 102 for displaying one or more generated images that are based on ultrasound image data received from the ultrasound imaging system 104 and/or the thermoacoustic data received from thermoacoustic imaging system 106.

The ultrasound imaging system 104 comprises one or more ultrasound transducer arrays 108 configured to emit sound waves 120 into the region of interest 116 of the subject 114. In this embodiment, the one or more ultrasound transducer arrays 108 are disconnectable from the ultrasound imaging system 104. The sound waves 120 directed into the region of interest 116 of the subject 114 echo off tissue within the region of interest 116, with different tissues reflecting varying degrees of sound. These echoes are received by the one or more ultrasound transducer arrays 108 and are processed by the ultrasound imaging system 104 before being communicated as ultrasound image data to the computing device 102 for further processing and for presentation and interpretation by an operator. In this embodiment, the ultrasound imaging system 104 utilizes B-mode ultrasound imaging techniques assuming a nominal speed of sound of 1,540 m/s. The B-mode image limits a field of view 118 form a conical shape extending from the ultrasound transducer arrays 108.

The thermoacoustic imaging system 106 comprises a processing unit comprising one or more processors, non-transitory system memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The thermoacoustic imaging system 106 also comprises at least one radio-frequency (RF) source 112 configured to generate short pulses of RF electromagnetic radiation that are directed into the region of interest 116 of the subject 114 to deliver energy to tissue within the region of interest 116 of the subject. The energy delivered to the tissue induces thermoacoustic pressure waves 124 and 138 that are detected by the thermoacoustic imaging system 106 using one or more thermoacoustic transducer arrays 110. The secondary object of interest (e.g., tumor) 132 also generates thermoacoustic pressure waves that are not shown in FIG. 1.

In one embodiment, the thermoacoustic imaging system 106 makes use of the one or more ultrasound transducer arrays 108 of the ultrasound imaging system 104 by disconnecting the one or more ultrasound transducer arrays 108 of the ultrasound imaging system 104 and connecting them to the thermoacoustic imaging system 106 and as such, coordinate mapping between ultrasound transducer arrays 108 is not required.

In one embodiment, the RF source 112 has a frequency between about 10 MHz and 100 GHz and has a pulse duration between about 0.1 nanoseconds and 10 microseconds. Acoustic pressure waves detected by the one or more thermoacoustic transducer arrays 110 are processed and communicated as thermoacoustic data to the computing device 102 for further processing and for presentation and interpretation by an operator.

In a separate embodiment, the thermoacoustic imaging system 106 could utilize separate thermoacoustic transducers from the ultrasound transducer arrays 108. Each transducer may have one or more transducer elements. Transducer elements may be characterized by transducer element specific kernels. Transducer elements may have the same specifications (e.g., center frequency), but other aspects may vary (e.g., bandwidth). Kernels may be utilized for these different properties.

In one embodiment, a user utilizes the computing device 102 to operate the ultrasound imaging system 104. The ultrasound imaging system 104 sends a signal to ultrasound transducer arrays 108, which sends sound waves 120 into subject 114 (the ultrasound transducer arrays 108 typically rest on the skin of the subject (e.g., patient)). The sound waves 120 reflect off of objects within the subject 114 and the ultrasound transducer arrays 108 receive the reflected sound waves to generate a B-mode image via the ultrasound imaging system 104. The extent of the B-mode image is conical in shape and is shown with B-mode image limits 118. The B-mode image gives the physical location of the region of interest 116 and boundary 126, enabling the computing device 102 to correlate data from the thermoacoustic imaging system 106 via the actual position on the subject 114 of the thermoacoustic transducer array 110 and RF emitter 112. Typically, once position coordinates are known, the ultrasound imaging system 104 can be turned off to eliminate potential interference with the thermoacoustic imaging system 106. The thermoacoustic imaging system then initiates the RF emitter 112 to send RF energy pulses 122 into the subject 114. The RF energy 122 pulses are absorbed in the region of interest 116. Within the region of interest 116, there are boundaries 126 and 140 between references 130 and an object of interest 128. The difference between RF energy absorbed in reference 130 and object of interest 128 creates thermoacoustic bipolar signals 124 and 138 emanating from boundary locations 134 and 136. Thermoacoustic transducer array 110 receives the thermoacoustic bipolar signals 124 and 138 and sends the resulting data to the thermoacoustic imaging system 106, which shares the data with the computing device 102.

In a thermoacoustic transducer optimization method, N-dimensional transforms (or impulse responses) are generated, and those responses are evaluated using metrics or compared to a more idealized system. By using fewer transducer elements than an idealized system, the system will determine how the feedback for the restricted amount of transducer elements compares in that particular configuration. A configuration of the design can be adjusted, and the system will again generate N-dimensional transforms (or impulse responses) to determine whether the adjusted configuration better achieves a desired response. This process is iterated until a desired configuration is achieved, such as a design that satisfies a particular threshold value for a metric.

In order to assess whether the tested configuration is an optimal design, the configuration may be compared to metrics or an ideal system. The metrics may be based on sensitivity, angles, frequency, etc. The metric can measure a quality of the impulse response without using a reference. For example, the metric may be based on how isotropic is a shape. In an ideal system comparison, the ideal system is measured to obtain the ideal result. An image of the tested configurations is then compared to an ideal image of the ideal system.

The processes described below are implemented using the hardware described with respect to FIG. 1. The processes may be performed by the computing device 102, thermoacoustic imaging system 106, or a combination of the computing device 102 and thermoacoustic imaging system 106. For example, a simulation and configuration of the transducer geometry 102 can be performed using the computing device or the thermoacoustic imaging system 106.

Figure 2:
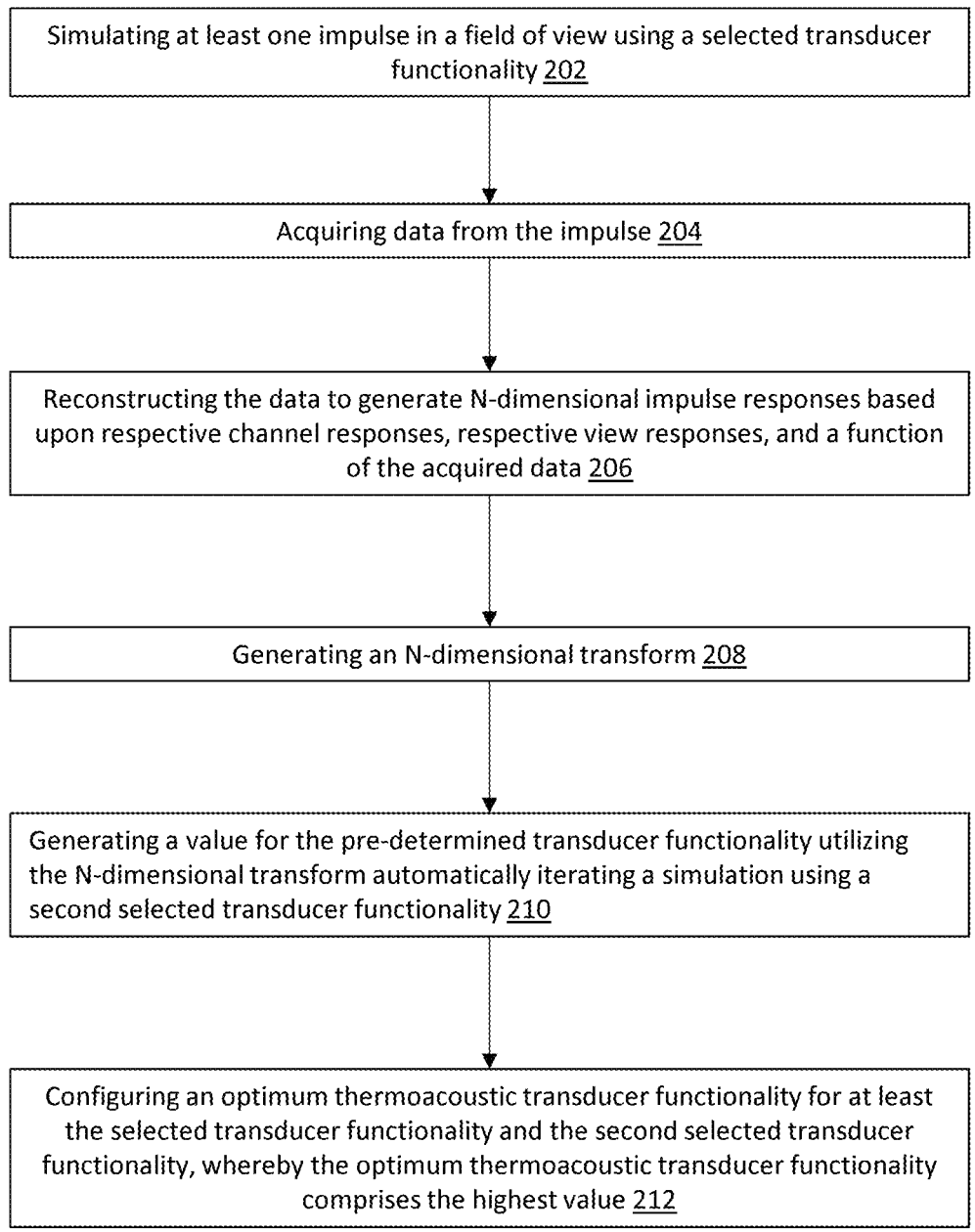
FIG. 2 shows a thermoacoustic transducer optimization method embodiment.

FIG. 2 shows a thermoacoustic transducer optimization method for selecting a pre-determined transducer geometry for the thermoacoustic imaging system, according to an embodiment. The transducer geometry may be selected or configured on a user interface. The transducer geometry may be dependent upon a number of transducer elements, a distribution of transducer elements, an orientation of transducer elements, and/or an offset axis of rotation.

In step 202, the thermoacoustic imaging system is utilized with the pre-determined transducer geometry to simulate at least one impulse in a field of view is generated by the thermoacoustic imaging system for a predetermined transducer geometry. For each transducer geometry, the simulation can include directing RF pulses toward a region of interest and inducing thermoacoustic signals from the region of interest.

In step 204, time-series data is acquired from the impulse.

In one optional configuration, each transducer element specific kernel is generated by estimating an impulse response for each transducer element, filtering the estimated impulse responses based upon prior transducer element knowledge, and applying one-dimensional noise and artifact reduction to the filtered estimated impulse responses. Prior transducer element knowledge can include a bandwidth of each transducer in the thermoacoustic imaging system, a center frequency of each transducer in the thermoacoustic imaging system, transducer directivity, a value derived from a noise test, or some combination thereof. Alternatively, filtering (e.g., linear filtering) or another baseline correction may be performed to address artifacts before applying the kernel.

The method may further deconvolve the time-series data with a transducer element specific kernel, then denoise and correct to generate a deconvolved corrected time-series data for that transducer element specific kernel. The deconvolving step can use linear processing to remove characteristics from measurements during the signal processing. Two-dimensional denoising and artifact correction algorithms are applied to generate corrected deconvolved time-series data. One-dimensional or two-dimensional filtering may be utilized to further improve a signal to noise ratio.

In step 206, the data is reconstructed (e.g., back-projected) to generate N-dimensional impulse responses based upon respective channel responses, respective view responses, and a function of the acquired data.

In step 208, N-dimensional transforms (or impulse responses) are generated. The N-dimensional transforms may generate a spatial frequency. Alternatively, the N-dimensional transforms may use K-space sampling. The N-dimensional transforms can utilize all or a subset of the data.

In step 210, the impulse response of each image is utilized to generate a value for the pre-determined transducer functionality. For example, a value representing a high spatial frequency is desired over a value representing a low spatial frequency. The value defines an absolute metric that measures a quality of the spatial frequency function without using a reference. Alternatively, the value defines a relative metric that utilizes an ideal transducer functionality.

In step 212, the value for the pre-determined transducer functionality is utilized to determine or configure an optimum thermoacoustic transducer functionality. The optimum thermoacoustic transducer functionality may comprise the selected transducer functionality having the highest value.

Figure 3A:
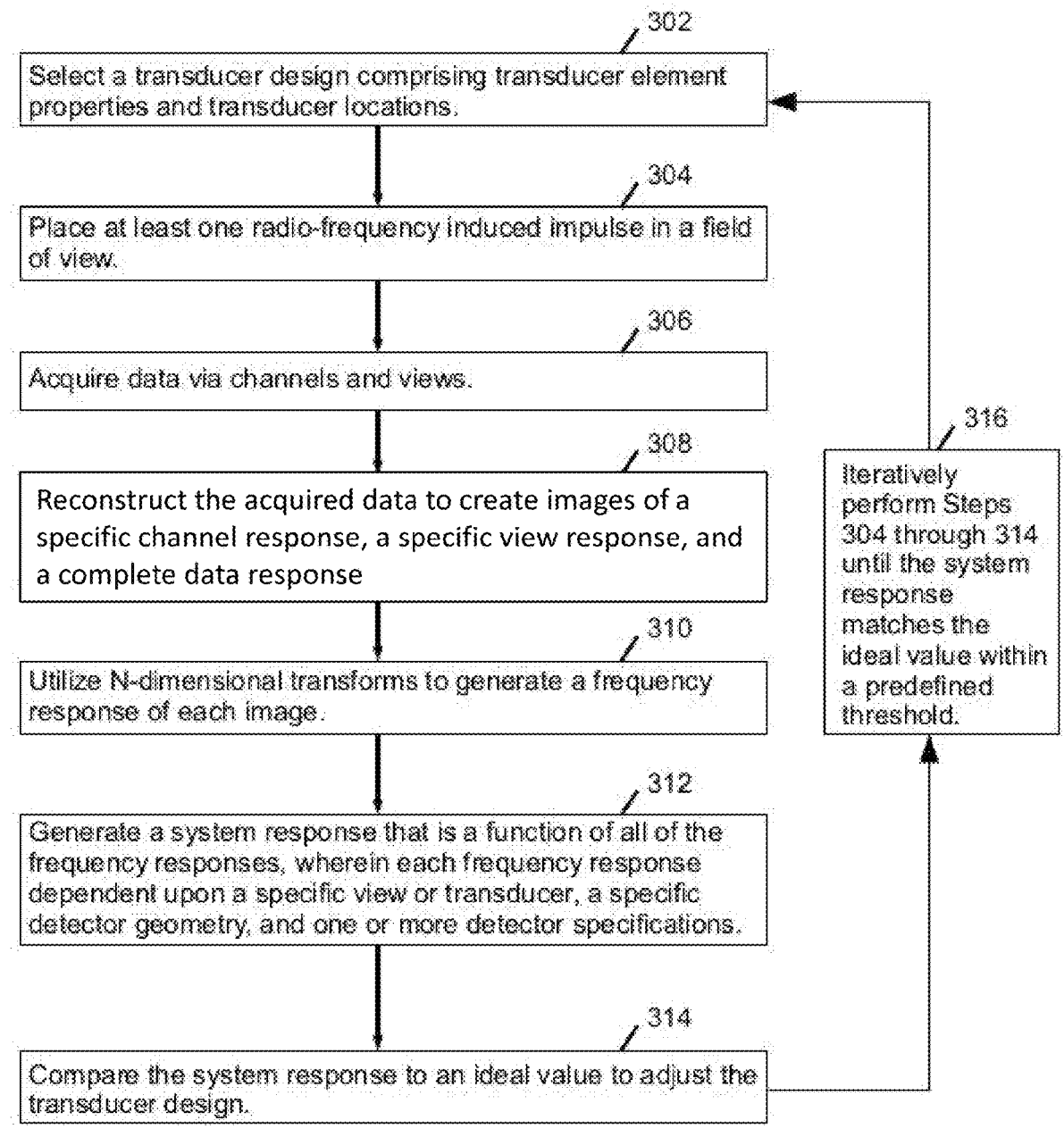
FIG. 3A shows a second thermoacoustic transducer optimization method embodiment.

FIG. 3A shows a second thermoacoustic transducer optimization method, according to another embodiment. In step 302, a transducer design comprising transducer element properties and transducer locations is selected. In step 304, at least one radio-frequency induced impulse is placed in a field of view. In step 306, data is acquired via channels and views. In step 308, the acquired data is reconstructed (e.g., back-projected) to create images of a specific channel response, a specific view response, and a complete data response. In step 310, N-dimensional transforms are generated for each image. In one configuration, the N-dimensional transforms may be utilized to generate a spatial frequency of each image. In step 312, a system response that is a function of all of the N-dimensional transforms is generated, wherein each frequency response is dependent upon a specific view or transducer, a specific detector geometry, and one or more detector specifications. In step 314, the system response is compared to an ideal value to adjust the transducer design.

In step 316, steps 304 through 314 are iteratively performed until the system response matches the ideal value within a predefined threshold. The system automatically varies the transducer design for each iteration within parameters set on the computing device or thermoacoustic imaging system. For example, if ten transducer elements can be added, then each iteration will consider a different distribution of those transducer elements, orientation of transducer elements, amount of transducer elements, and/or an offset axis of rotation. The iterations may terminate once the response satisfies certain criteria or upon reaching a defined number of iterations. For example, a spatial frequency can be mapped into a value (e.g., in a range from 0.0 to 1.0 for how isotropic) and compared to a threshold (e.g., value is 0.5 and threshold set at 0.8). The termination can rely upon satisfying more than one threshold.

Figure 3B:
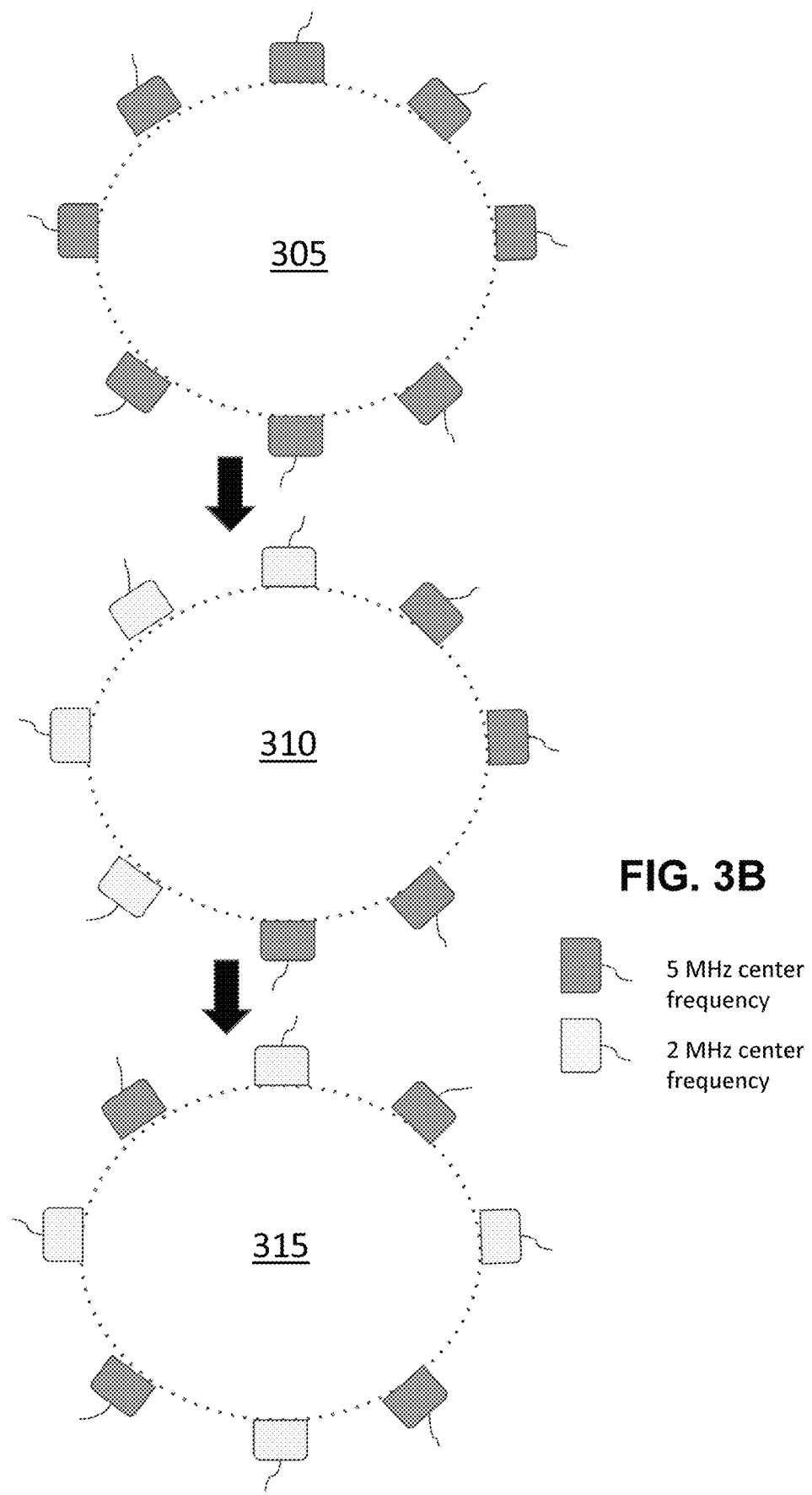
FIGS. 3B and 3C show changes to transducer elements, according to an embodiment.
Figure 3C:
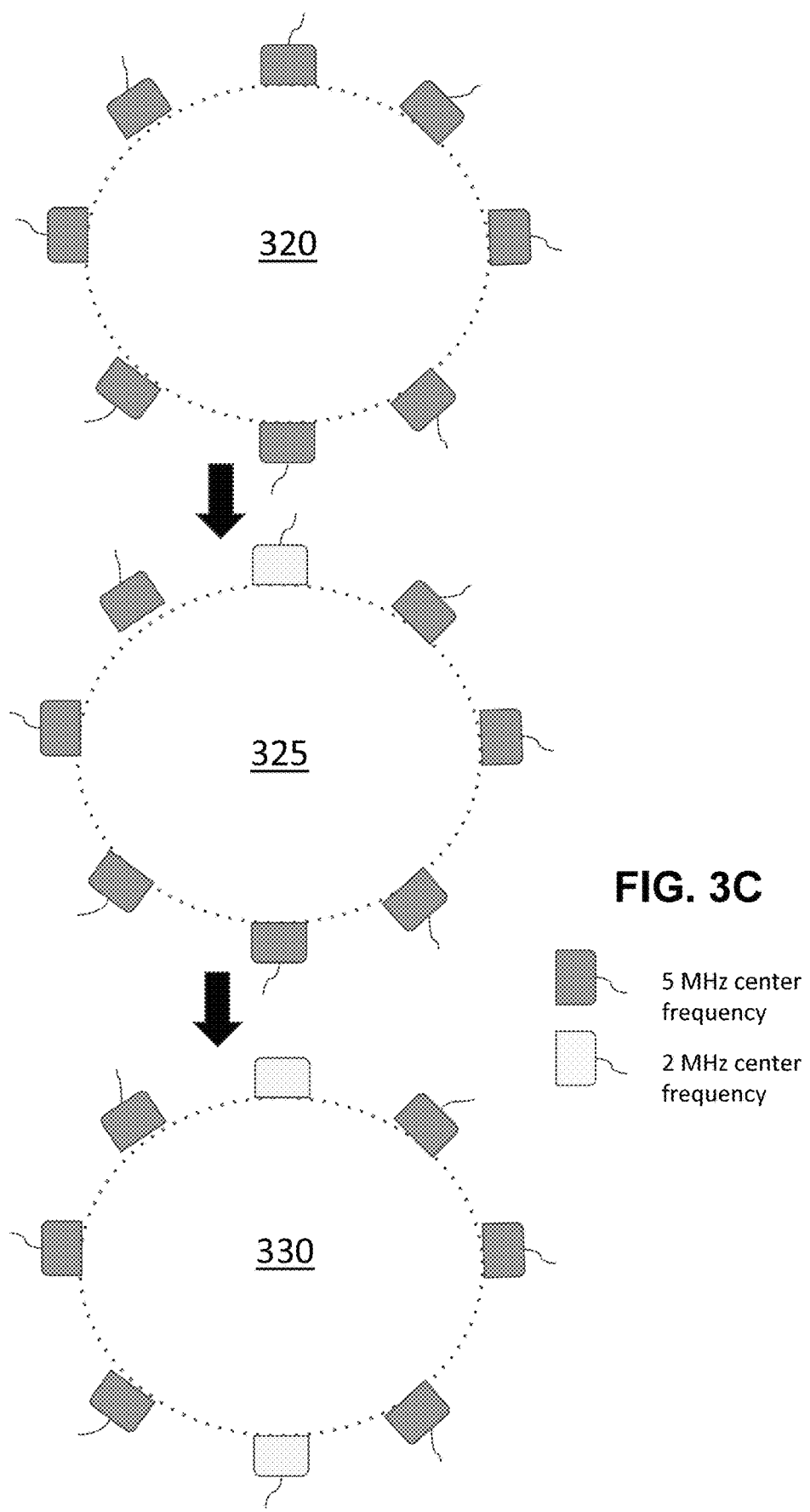

FIGS. 3B and 3C show examples of the iterative process using various configurations of 2 MHz and 5 MHz transducer elements in a ring (circular) design. Transducer elements can be reconfigured in groups of one or more in each iteration. In this embodiment, the transducer elements are changed from a first frequency to a second frequency. However, it is also intended that other characteristics of the transducer elements can change as well as the distribution and positioning of the transducer elements.

In FIG. 3B, a first configuration 305 has all 5 MHz transducer elements. After a first iteration, some of the transducer elements in configuration 310 has some 2 MHz transducer elements and some 5 MHz transducer elements. After a second iteration, the distribution of the 2 MHz and 5 MHz transducer elements changes to an alternating pattern in configuration 315.

Transducer elements can be changed individually in each iteration. In FIG. 3C, a first configuration 320 has all 5 MHz transducer elements. After a first iteration, configuration 325 has one 2 MHz transducer element replacing a 5 MHz transducer element. After a second iteration, configuration 330 has a second 2 MHz transducer element replacing another 5 MHz transducer element.

The following figures show examples of how various method embodiments can be used. The transducer geometries corresponding to the embodiments can affect the image quality. In one example, a bowl geometry with 128 transducers is given as the existing design. Transducers are distributed on the bowl's inner surface in a spiral pattern. By using the described method, new geometries can be designed and compared using simulations.

Figure 4A:
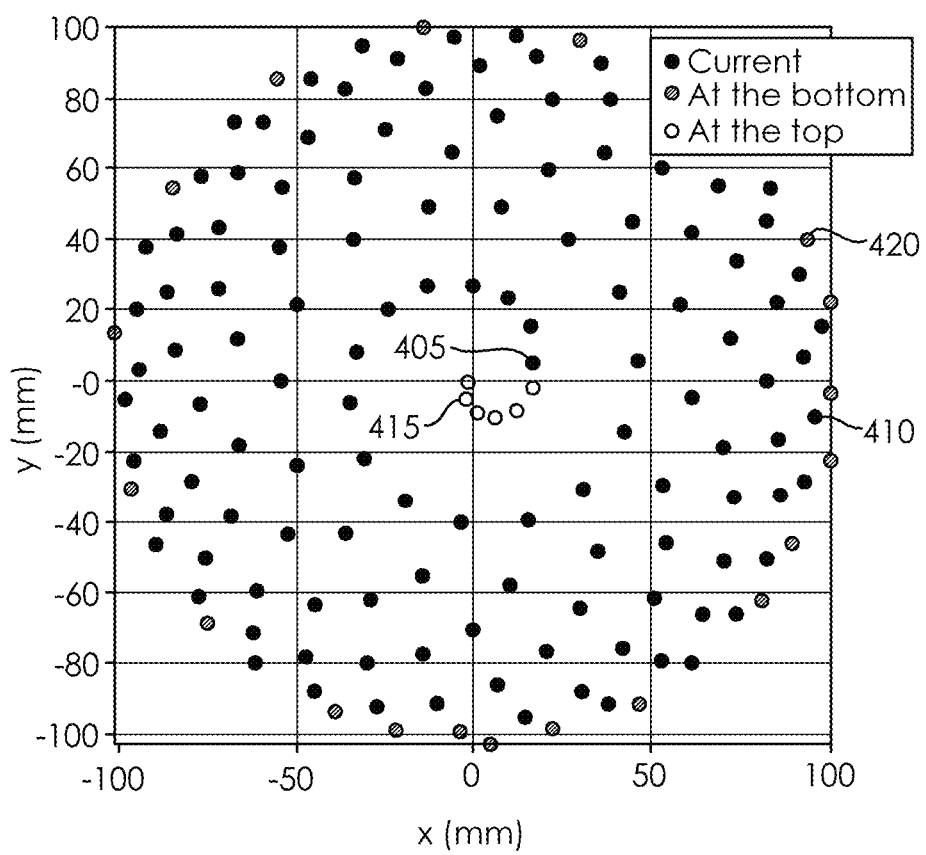
FIGS. 4A-4C show locations of current and added transducer elements, according to an embodiment.
Figure 4B:
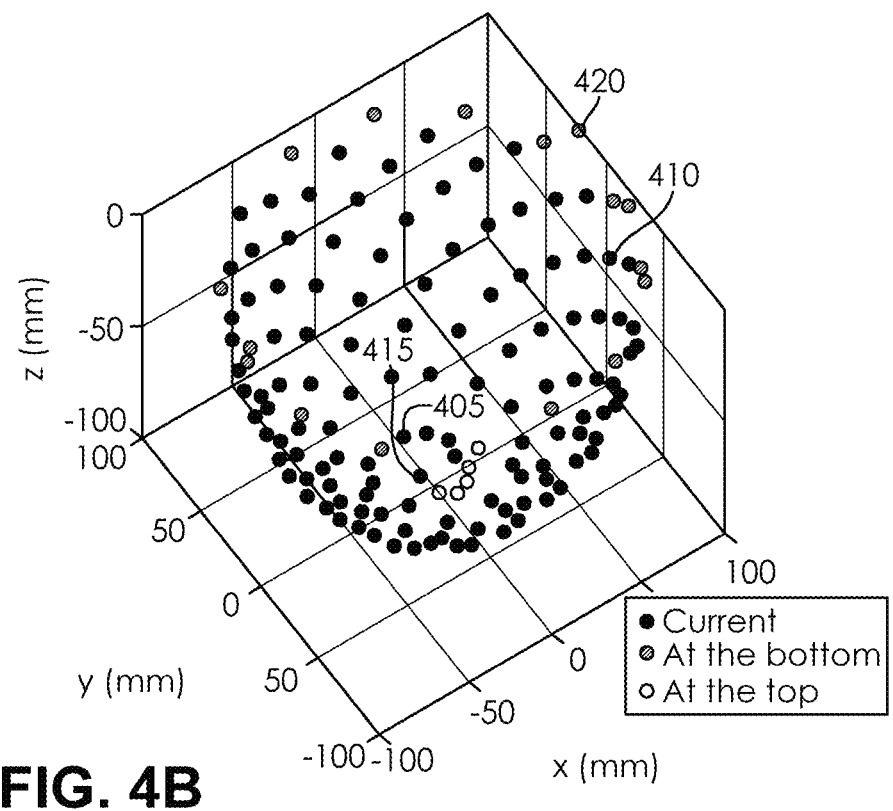
Figure 4C:
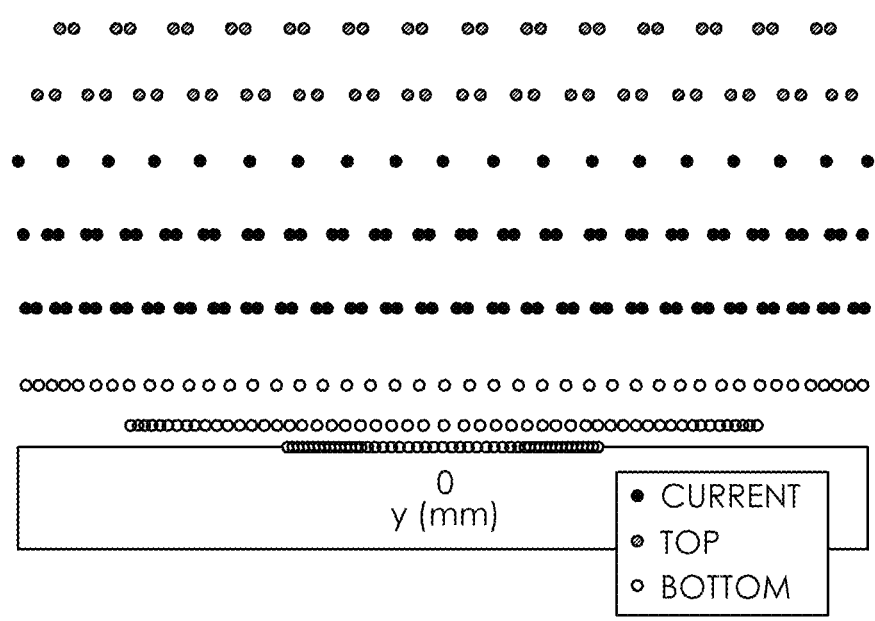

FIGS. 4A-4C show locations of current and added transducers in a bowl (hemisphere) geometry, whereby two bowls can be configured to enclose an object to seek a better sampling of that object. FIG. 4A depicts a top view of the bowl, where transducers are arranged in a helical or spiral pattern extending from a bottom of the bowl (e.g., transducer 405) to a top of the bowl (e.g., transducer 410). FIG. 4B depicts a perspective view of the bowl. FIG. 4C shows a zoomed side view near the bottom of the bowl. In addition to the current 128 transducers in the bowl, extra transducers were added to improve the sampling condition. As described above, locations of transducers were determined in a way that is consistent with the current distribution (e.g., helical spiral pattern). Six transducers 415 were added at the bottom of the bowl, but due to physical constraints, not all six transducers can be placed. However, for the purpose of illustration, a configuration with all six transducers is shown. 17 transducers 420 were added near the top of the bowl. Adding all of these transducers would require changing the shape of the bowl. Such physical modification may not be possible or desired in some cases. These limitations may be considered in the design process. For the purpose of illustration, a configuration with all 17 transducers 420 is shown. Utilizing all of these transducers, this configuration assumed an ideal impulse response.

A three-dimensional phantom can be constructed using two-dimensional cross-sectional slices. When performing a simulation to construct the three-dimensional phantom, a particular configuration of transducer elements may have a better resolution in one direction than another. Each of FIGS. 5A-5E shows three cross-sectional slices after acquiring an image and doing a reconstruction.

Figure 5A:
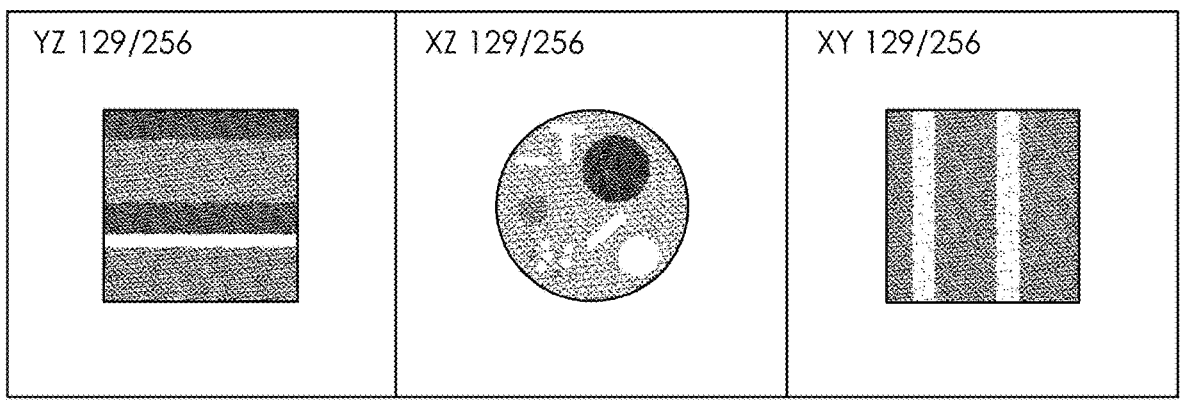
FIGS. 5A-5E show reconstructed images from complete 4 PI steradian sampling, according to an embodiment.
Figure 5B:
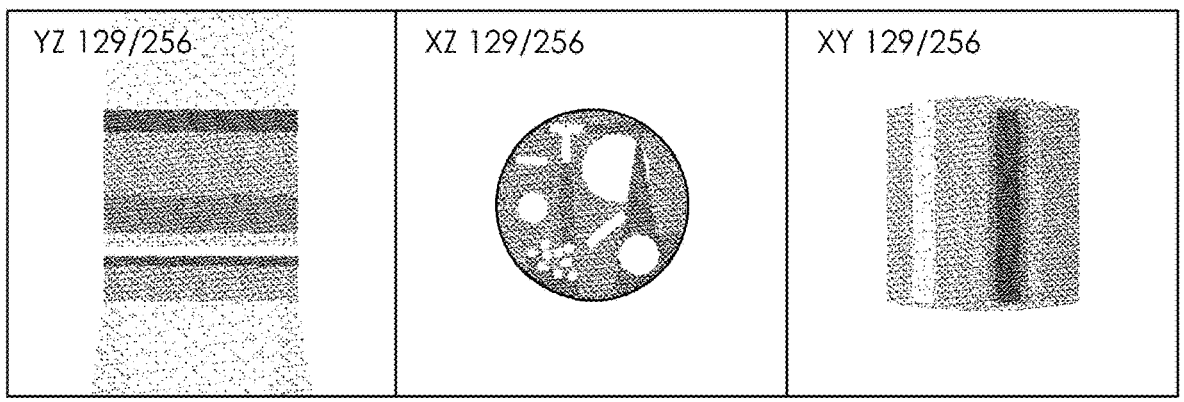

FIG. 5A shows a digital phantom used for a simulation. FIG. 5B shows a reference image of the initial design, whereby 128 transducer elements (channels) were distributed on a hemisphere (bowl configuration).

Figure 5C:
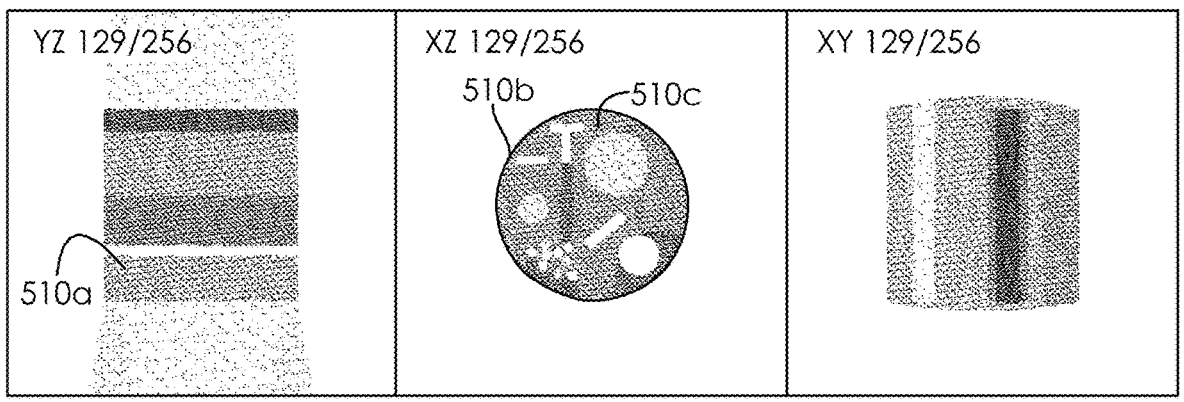
Figure 5D:
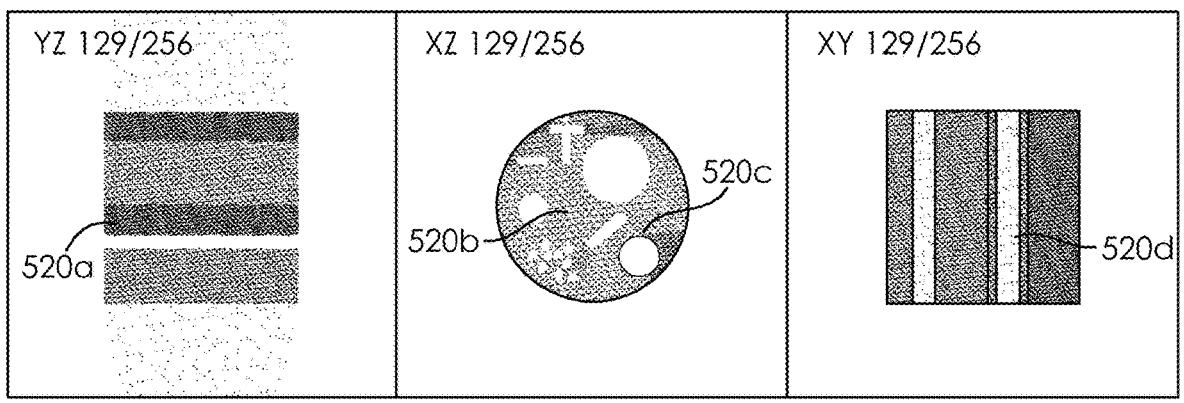
Figure 5E:
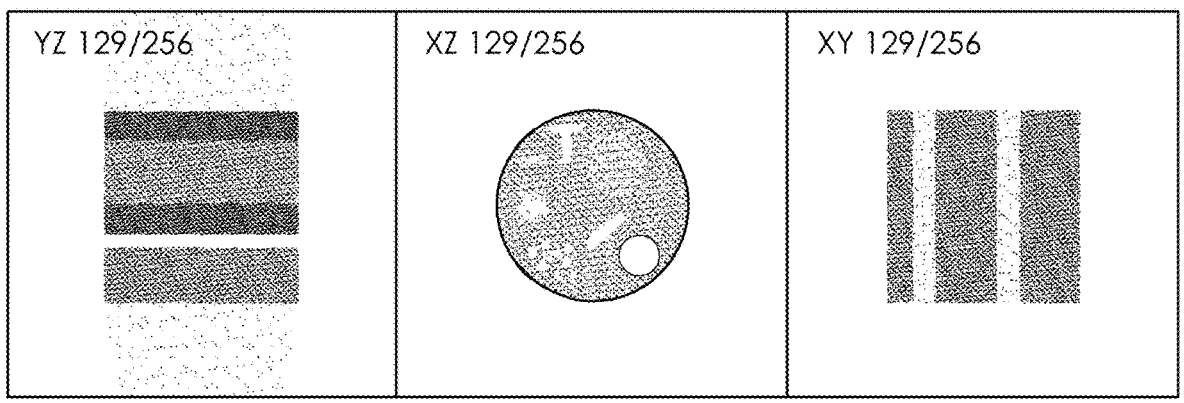

Adding transducer elements improved reconstructed images. FIG. 5C shows an image upon adding three transducer elements to the bottom of the hemisphere. Improvements 510a, 510b, 510c are shown with respect to the reference image of FIG. 5B. FIG. 5D adds 23 transducer elements at the top of the hemisphere. Improvements 520a, 520b, 520c, 520d are shown with respect to the reference image of FIG. 5B. FIG. 5E adds three transducer elements to the bottom of the hemisphere and 23 transducer elements at the top of the hemisphere for a full hemisphere sampling. Adding more transducers on the top and bottom of the hemisphere can give a more accurate image with more detail and fewer artifacts.

By varying the configurations, the test image can be compared to the ideal image to determine if quality has been degraded too much by removing or redistributing transducer elements. The configuration in FIG. 5E may be desired because it has the most transducer elements, but due to some constraints, it may not be feasible. A comparison of the results from FIGS. 5C, 5D, and 5E allow for a configuration that optimizes the transducer elements in view of the responses. In one example, if the configuration of FIG. 5E is not feasible, the configuration of FIG. 5D may satisfy any threshold requirements or have substantial similarity to a particular result (e.g., the digital phantom of FIG. 5A).

Figure 6:
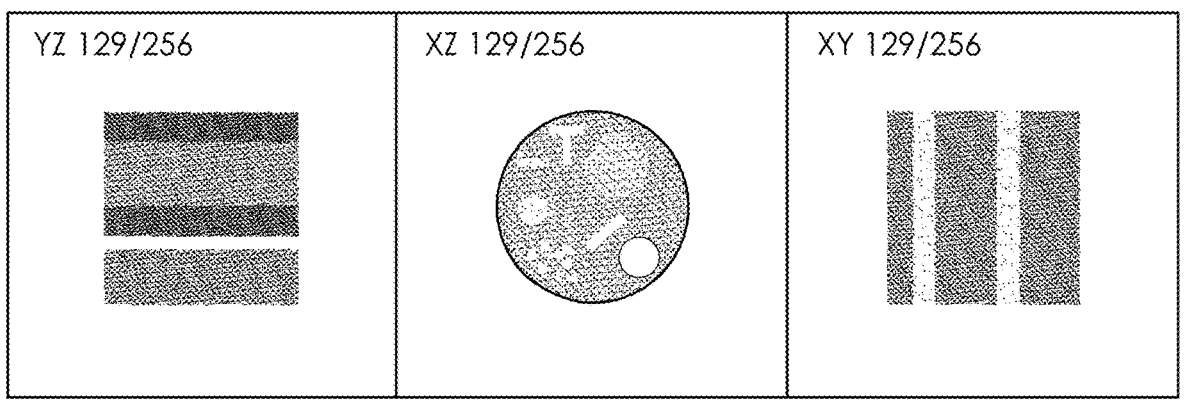
FIG. 6 shows reconstructed images from complete "ball" sampling, according to an embodiment.

FIG. 6 shows reconstructed images from images slices for a complete "ball" sampling. 302 transducer elements covering both the top and bottom hemispheres (bowls) were simulated, which includes the current 128 transducer elements in each hemisphere as well as 17 added transducer elements at the top and 6 added transducer elements at the bottom of each hemisphere. As described above, there may be some physical or other constraints that prevent such a design. However, for the purpose of illustration, the results with the ball shaped geometry are presented. The z-slices are now "even." So the sampling itself is another reason for the gradation artifact. Some residual artifacts may come from the reconstruction filter and weighting factors used during the reconstruction process (e.g., Shepp-and-Logan filter). Available reconstruction and signal processing techniques can also become constraints for the transducer geometry design. This image shows an ideal configuration that utilizes 302 transducer elements. Images based upon fewer transducer elements (e.g., shown in FIG. 5A) can be compared to the ideal image. A functionality having the best result compared to the ideal image will be selected for configuring the transducer.

Figure 7A:
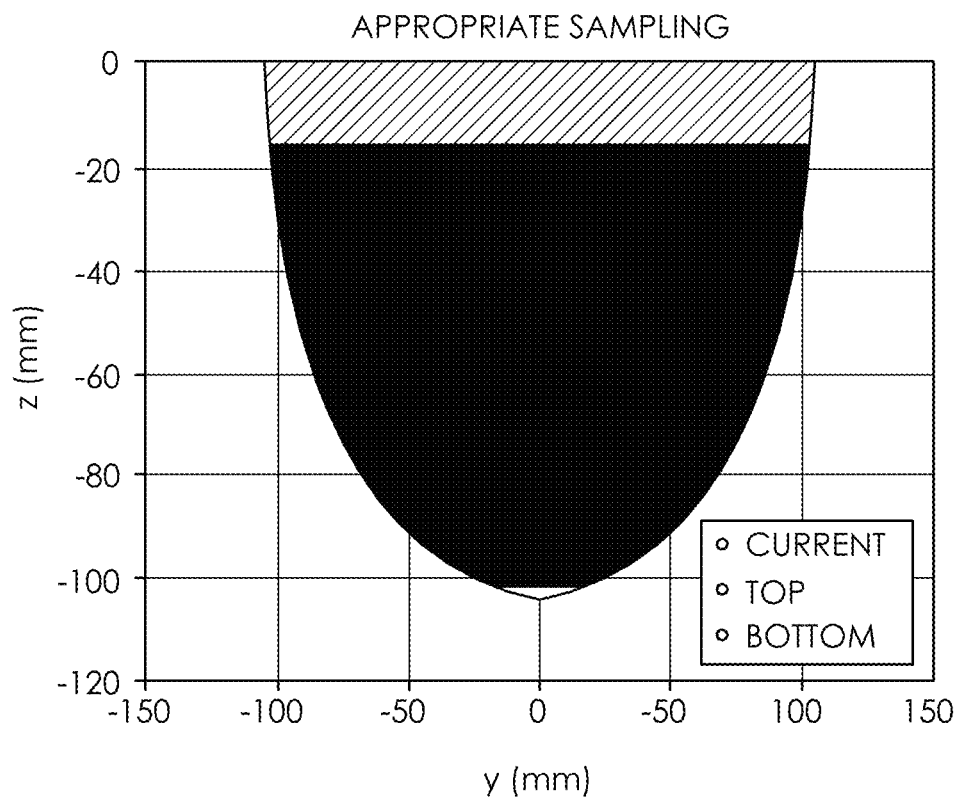
FIGS. 7A-7B show the sampling by rotating a bowl, according to an embodiment.
Figure 7B:
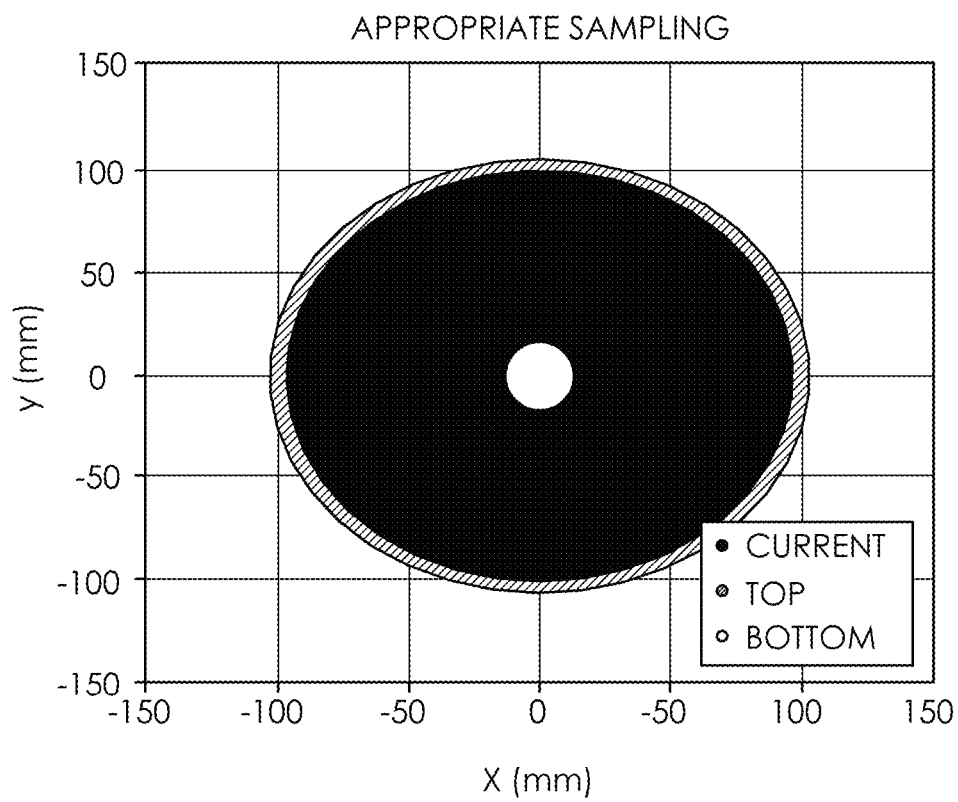

The transducer functionality may be dependent upon a motion of transducer elements, wherein the motion of transducer elements comprises a rotational angle and an angle step size. FIGS. 7A-7B show a sampling by rotating (spinning) the bowl (120 views, 3 degree step size). FIGS. 7A-7B show a new transducer element arrangement, such as the configuration shown in FIGS. 4A-4B. FIG. 7A shows a side view. FIG. 7B shows a top view. FIGS. 7A-7B show a sampling from the transducer elements when the bowl is rotated, allowing the transducer elements to cover a wider area.

A transducer functionality can vary by reconfiguring an axis of rotation using an offset. For example, in a bowl (hemisphere) configuration, there may not be a transducer element at the bottom of the bowl, so the sampling may be incomplete. Even though more transducer elements can be added in the different iterations, a laser located at the bottom of the bowl prevents a complete sampling. Missing a sampling from the bottom can lead to artifacts and an incorrect reconstruction.

The scanning geometry can improve the sampling condition without adding more transducer elements. If the lowest transducer element is used as an axis of rotation, for example, then that lowest transducer element becomes the "effective bottom" of the bowl. As the methods continue to iterate, various points in the bowl may be used for the axis of rotation. The offset axis of rotation is another parameter that can be varied in determining which geometries satisfy the desired output. The offset can also be used in combination with various rotation angles.

Figure 8A:
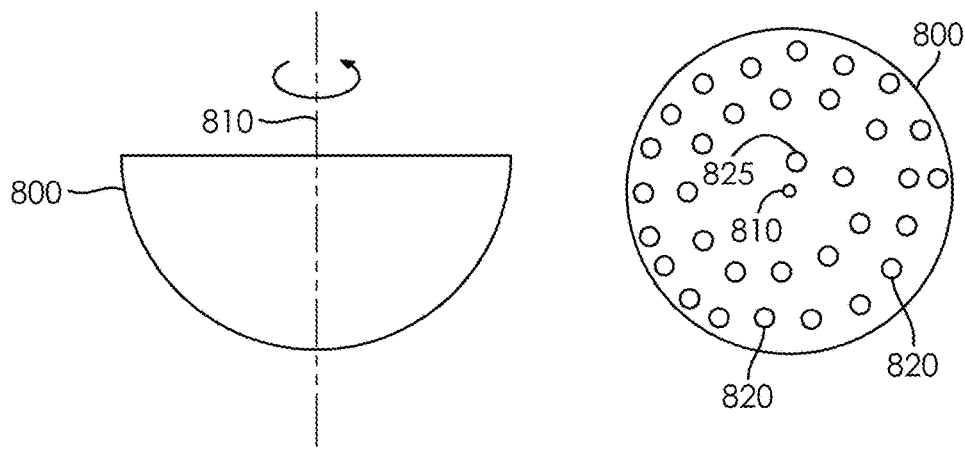
FIG. 8A shows a bowl having a central axis of rotation, according to an embodiment.

Referring to FIG. 8A, a bowl 800 is shown having an axis of rotation 810 through a bottom of the bowl 800. Bowl 800 has transducer elements 820, including a lowest transducer element 825.

Figure 8B:
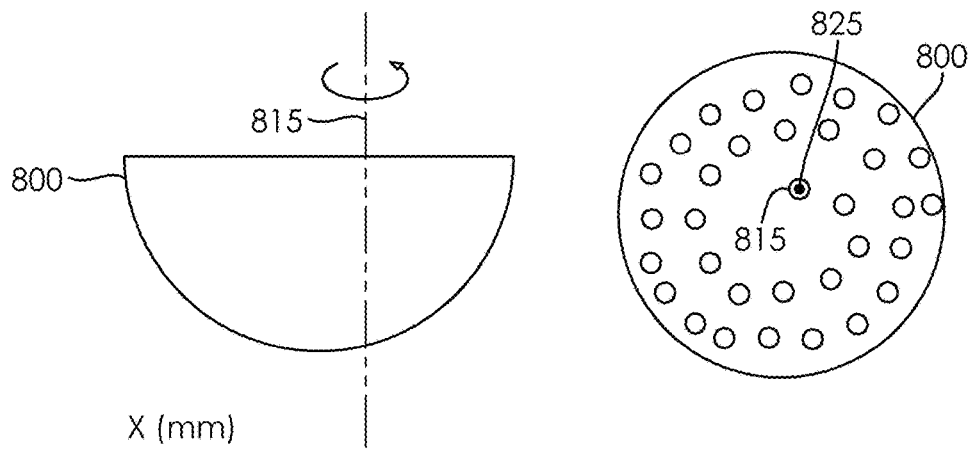
FIG. 8B shows a bowl having an offset axis of rotation, according to an embodiment.

In FIG. 8B, a new axis of rotation 815 has moved from a bottom of the bowl 800 to the lowest transducer element 825. The distance between the new axis of rotation 815 and the axis of rotation 810 at the bottom of the bowl 800 is an offset.

Figure 8C:
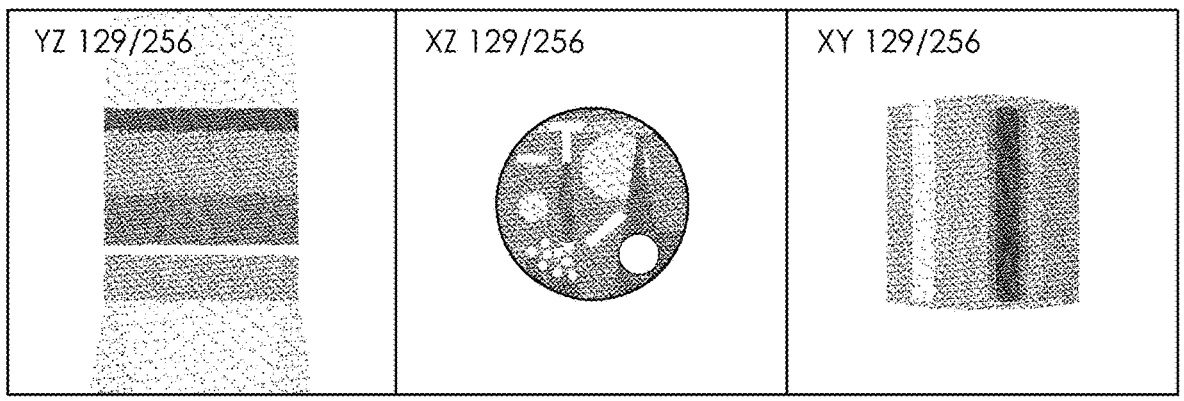
FIG. 8C shows a reconstructed image using an offset axis of rotation, according to an embodiment.

This new configuration resulted in an improvement to reconstructed images, such as a comparison of the reference image in FIG. 5B to the reconstructed image in FIG. 8C produced using the offset axis of rotation.

Although embodiments have been described above with reference to the accompanying drawings, those of skill in the art will appreciate that variations and modifications may be made without departing from the scope thereof as defined by the appended claims.

What is claimed is:

1. A method for determining a thermoacoustic transducer functionality of a thermoacoustic imaging system, wherein the thermoacoustic imaging system comprises at least one radio-frequency source, at least one thermoacoustic transducer, and at least one processor, the method comprising:
   (A) placing an object in a field of view;
   (B) generating at least one impulse within the field of view, using the thermoacoustic imaging system with a first selected transducer functionality, wherein the first selected transducer functionality defines transducer geometry, arrangement of transducer elements, or distribution of transducer dements, further wherein the first selected transducer functionality works with a selected configuration of transducer elements based upon transducer elements' center-frequency and bandwidth, further wherein the at least one impulse is generated by directing radio-frequency energy pulses toward the field of view and inducing thermoacoustic signals from the object;
   (C) acquiring, by the thermoacoustic imaging system, data from the at least one impulse;
   (D) reconstructing, by the thermoacoustic imaging system, the acquired data to generate N-dimensional impulse responses based upon respective channel responses, respective view responses, and a function of the acquired data;
   (E) generating, by the thermoacoustic imaging system, an N-dimensional transform based upon the N-dimensional impulse responses;
   (F) utilizing, by the thermoacoustic imaging system, the N-dimensional transform to generate an N-dimensional value that corresponds to a frequency response that is a function of the first selected transducer functionality;
   (G) iteratively performing steps (A) through (F) with different selected transducer functionalities substituted for the first selected transducer functionality, wherein the different selected transducer functionalities are different from the selected transducer elements' center-frequency and bandwidth and are also different in one of a different transducer geometry, arrangement of transducer elements, or distribution of transducer elements; and
   (H) configuring, by the thermoacoustic imaging system, a final thermoacoustic transducer functionality based upon the generated N-dimensional values.

2. The method of claim 1, further comprising denoising and correcting, by the thermoacoustic imaging system, to generate corrected time-series data for each transducer element.

3. The method of claim 2, further comprising: deconvolving the corrected time-series data; and applying, by the thermoacoustic imaging system, 2-D denoising and artifact correction algorithms to generate corrected deconvolved time-series data.

4. The method of claim 1, further comprising generating transducer element specific kernels by steps comprising:
   estimating an impulse response for each transducer element;
   filtering the estimated impulse response of each element based upon prior transducer element knowledge; and
   applying 1-dimensional noise and artifact reduction to the filtered estimated impulse response of each element.

5. The method of claim 4, wherein the prior transducer element knowledge is selected from a group consisting of a bandwidth of each transducer in the thermoacoustic imaging system, a center frequency of each transducer in the thermoacoustic imaging system, a transducer directivity, and/or a value derived from a noise test.

6. The method of claim 1, wherein the N-dimensional transform utilizes a subset of the acquired data.

7. The method of claim 1, wherein the N-dimensional value for the first selected transducer functionality and the N-dimensional value for a second selected transducer functionality define an absolute metric which measures a quality of the N-dimensional transforms.

* * * * *